United States Patent [19]

Wallach

[11] Patent Number: 4,942,038
[45] Date of Patent: Jul. 17, 1990

[54] ENCAPSULATED HUMECTANT

[75] Inventor: Donald F. H. Wallach, Brookline, Mass.

[73] Assignee: Micro Vesicular Systems, Inc., Nashua, N.H.

[21] Appl. No.: 234,309

[22] Filed: Aug. 19, 1988

Related U.S. Application Data

[63] Continuation-in-part of Ser. No. 25,525, Mar. 13, 1987, abandoned, and a continuation-in-part of Ser. No. 78,658, Jul. 28, 1987, Pat. No. 4,885,090, and a continuation-in-part of Ser. No. 124,824, Nov. 24, 1987, Pat. No. 4,917,951, and a continuation-in-part of Ser. No. 157,571, Mar. 3, 1988, Pat. No. 4,911,928.

[51] Int. Cl.$^5$ .............. A61K 7/06; A61K 7/075; A61K 9/127; C09K 3/00
[52] U.S. Cl. .............. 424/450; 252/174.13; 252/194; 252/DIG. 13; 424/70; 424/71; 424/DIG. 4; 428/402.2; 514/880; 514/881
[58] Field of Search .......... 252/194, DIG. 13, 174.13; 428/402.2; 424/70, 450, DIG. 4, 71; 514/880, 881

[56] References Cited

U.S. PATENT DOCUMENTS

| | | | |
|---|---|---|---|
| B 438,048 | 3/1976 | Fogel et al. | 424/70 |
| 3,957,971 | 5/1976 | Oleniacz | 424/70 |
| 4,002,734 | 1/1977 | Pickford | 424/70 X |
| 4,126,674 | 11/1978 | Mausner | 428/402.2 X |
| 4,133,874 | 1/1979 | Miller et al. | 424/450 |
| 4,217,344 | 8/1980 | Vanlerberghe et al. | 424/60 |
| 4,235,871 | 11/1980 | Papahadjopoulos et al. | 424/450 |
| 4,241,046 | 12/1980 | Papahadjopoulos et al. | 424/450 X |
| 4,247,411 | 1/1981 | Vanlerberghe et al. | 424/450 X |
| 4,331,654 | 5/1982 | Morris | 424/450 |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,668,434 | 5/1987 | Bowman | 424/70 X |
| 4,690,818 | 9/1987 | Puchalski, Jr. et al. | 424/70 |
| 4,692,433 | 9/1987 | Hostetler et al. | 514/12 |
| 4,695,554 | 9/1987 | O'Connell et al. | 436/528 |
| 4,772,471 | 9/1988 | Vanlerberghe et al. | 424/450 |
| 4,837,019 | 6/1989 | Georgalas et al. | 424/DIG. 13 |

FOREIGN PATENT DOCUMENTS

| | | |
|---|---|---|
| 0032578 | 7/1984 | European Pat. Off. |
| 0167825 | 6/1985 | European Pat. Off. |
| 3410602 | 9/1984 | Fed. Rep. of Germany |
| 59-106423 | 6/1984 | Japan |
| 61-207324 | 9/1986 | Japan |
| 85/01440 | 4/1985 | PCT Int'l Appl. |
| 87/06499 | 11/1987 | PCT Int'l Appl. |
| 1539625 | 6/1976 | United Kingdom |
| 2147263 | 5/1985 | United Kingdom |

OTHER PUBLICATIONS

McCutheon's Detergents and Emulsifiers, 1973, N. American Ed., Publ. by McCutcheon's Division, Allured Publ. Corp., Ridgewood, N.J. (1973), p. 27.
Bangham et al. (1965), J. Mol. Biol., 238–252.
Gregoriadis (1976), The New England Journal of Medicine, 295:704–710.
Szoka, Jr. (1978), Proc. Natl. Acad. Sci. USA, 75:4194–4198.
Philippot et al. (1983), Biochimica et Biophysica Acta., 734:137–143.
"Liposomes", Edited by Marc J. Ostro, The Liposome Co., Princeton, N.J., Marcel Dekker, Inc., New York, pp. 246–249 (1983).
Ribier et al. (1984), Cottoids and Surfaces, 10:155–161.
Baillie et al. (1985), J. Pharm. Pharmacol., 37:863–868.
Philippot et al. (1985), Biochimica et Biophysica Acta, 821:79–84.
"Methods de Preparation des Liposomes", Dousset and Douste-Blazy, Les Liposomes, Puisieux and Delattre, Eds., Techniques et Documentation la Voisier Paris, pp. 41–72 (1985).
"Problemes Technologiques Poses par l'Utilisation des Liposomes Comme Vecteurs de Substances Medicamenteuses, Encapsulation, Sterilisation, Conservation", Puisieux and Poly, Les Liposomes, Puisieux and Delattre, Eds., Techniques et Documentation la Voisier Paris, pp. 73–113 (1985).
"Les Niosomes", Handjani-Vila et al., Les Liposomes, Puisieux and Delattre, Eds., Techniques et Documentation la Voisier Paris, pp. 297–313 (1985).
Baillie et al. (1986), J. Pharm. Pharmacol., 38:502–505.

Primary Examiner—Richard D. Lovering
Attorney, Agent, or Firm—Lahive & Cockfield

[57] ABSTRACT

A new humectant for animal care product use having a moisturizer encapsulated in a lipid vesicle has been developed. The humectant is particularly useful as an additive to shampoos or cream rinses.

19 Claims, No Drawings

ENCAPSULATED HUMECTANT

REFERENCE TO RELATED APPLICATIONS

This application is a continuation-in-part to U.S. Patent Application Ser. No. 025,525 entitled, "Method of Producing High Aqueous Volume Multilamellar Vesicles," filed Mar. 13, 1987, now abandoned U.S. Patent Application Ser. No. 078,658 entitled, "Method of Producing High Aqueous Volume Multilamellar Vesicles," filed July 28, 1987, now U.S. Pat. No. 4,885,090, U.S. Patent Application Ser. No. 124,824 entitled, "Lipid Vesicles Formed of Surfactants and Steroids," filed Nov. 24, 1987, and now U.S. Pat. No. 4,917,951 and U.S. Patent Application Ser. No. 157,571 entitled, "Paucilamellar Lipid Vesicles," filed Mar. 3, 1988 and now U.S. Pat. No. 4,911,928.

BACKGROUND OF THE INVENTION

The present invention relates to humectants or moisturizers for personal or animal care products which are encapsulated in lipid vesicles. Lipid vesicle encapsulation provides controlled delivery and permits use of incompatible ingredients. The humectant of the invention is particularly useful as a moisturizer for external use, e.g., as an additive in medicated shampoos.

Phospholipids are the basis of most lipid vesicles tried to date because of their chemical similarity to the materials forming natural membranes. However, the high cost of purified phospholipids has limited their usefulness to preparations which could justify the large expenditure. Humectants for external use, e.g., shampoos, cream rinses, skin creams, and other external human or animal use, do not have a sufficiently high cost to make encapsulation with phospholipids economically feasible.

Surfactants and other nonphospholipid vesicles make areas which heretofore fiscally infeasible now possible. For example, L'Oreal has a "niosome" line of products which is based on nonphospholipid materials, and the present inventor and others at Micro Vesicular Systems have developed techniques for formation and utilization of nonphospholipid materials which yield results that were considered impossible only a few years ago. These new techniques and materials make everyday use of lipid vesicles a reality.

Accordingly, an object of the invention is to provide lipid vesicles which can encapsulate moisturizing materials to act as humectants in animal care products.

Another object of the invention is to provide encapsulated moisturizers for personal care products.

A further object of the invention is to provide a humectant in medicated external preparations for human and animal use.

These and other objects and features of the invention will be apparent from the following description and the claims.

SUMMARY OF THE INVENTION

The present invention features humectants formed of moisturizers encapsulated in paucilamellar lipid vesicles. The invention further features shampoos and cream rinses made using the lipid vesicle encapsulated humectant. The invention is based, in part, on the discovery that encapsulating a moisturizer in a lipid vesicle provides excellent humectant properties, with both the encapsulated moisturizer and the lipid vesicle itself having the moisturizing properties.

The humectant of the invention for external animal care products is formed, primarily, of a moisturizer encapsulated in a paucilamellar lipid vesicle. The paucilamellar lipid vesicle provides greater stability than a unilamellar lipid vesicle while allowing greater volume of moisturizer and surrounding water than is available from classic multilamellar lipid vesicles. Preferred non-phospholipid surfactants which form the major component of the paucilamellar lipid vesicles of the invention are polyoxyethylene ethers, particularly those selected from a group consisting polyoxyethylene lauryl ethers and polyoxyethylene cetyl ethers, glycerol monostearate, glycerol monooleate, and polyoxyethylene sorbitan oleates, stearates and palmitates. The lipid vesicle may also include a sterol, e.g., cholesterol, its chemical analogs, and its active fragments; and charge producing agents such as oleic acid or quaternary ammonium compounds. In addition, mineral oil, which acts as an osmotic pressure modifying agent, may be encapsulated in the vesicles for the encapsulated moisturizer.

The encapsulated humectant can be used in a number of different animal care products. Shampoos, moisturizing sprays, and cream rinses which contain the encapsulated humectant and, possibly, an active hair conditioning or a medicated agent, are also considered part of the present invention. Examples of these shampoos with medicated agents include coal tar shampoo, salicylic acid-sulphur shampoos, and benzoyl peroxide shampoos.

Although any materials which are useful in the manufacture of paucilamellar lipid vesicles may be used, (see United States Patent Application Ser. No. 157,571 now U.S. Pat. No. 4,911,928, assigned to the assignee of the present application and incorporated herein by reference, for additional materials), one preferred paucilamellar lipid vesicle is made of polyoxyethylene 2-cetyl ether (tradename BRIJ 52, ICI Americas) blended with cholesterol and a small amount of oleic acid as a charge producing agent. Although the ratio of the ingredients can vary, a 100:33:1 ratio of surfactant:sterol:charge producing agent has proved effective in manufacture of the encapsulated humectant of the invention.

DESCRIPTION OF THE INVENTION

The present humectant or encapsulated moisturizer can be used in a spray form with a variety of carriers, or blended into a shampoo or cream rinse to provide moisturizing when the vesicles are ruptured or distorted, e.g., during vigorous rubbing. The lipid vesicles also act as a moisturizer. These lipid vesicles are relatively sturdy, normally retaining their vesicle form during storage. The vesicles are as a barrier, separating the encapsulated moisturizer from the carrier. This permits the use of materials which otherwise may not be compatible in the same product.

As noted, a variety of nonphospholipid surfactants are useful in preparing the lipid vesicles of the invention. Examples of these surfactants include polyoxyethylene lauric, myristic, cetyl, stearic, and oleic acid esters; lauric, myristic, cetyl, unsaturated octadecyl, and unsaturated eicodienoic polyoxyethylene ethers; caprylic, lauric, myristic, and linoleic diethanolamines; glucosamine, galactosamine, and N-methylglucamine long-chain acyl hexosamides; long-chain acyl amino acid amides; polyoxyethylene sorbitan mono- and trioleates, palmitates and stearates: polyoxyethylene glyceryl monostearate; glycerol monostearate; and qlycerol monooleate. Additional nonphospholipid surfactants also may be useful in the invention. The only requirement for these materials is that they form stable paucilamellar lipid vesicles which show high water uptake and good mechanical stability.

A variety of moisturizers can be used in the invention but aqueous-soluble or suspendable moisturizers are preferred. The high aqueous volume uptake properties of the paucilamellar lipid vesicles used in this invention permit concentrated doses of the moisturizer to be delivered to the hair follicles of the animal to which the moisturizer is applied. In addition, the trapped water and lipids themselves have moisturizing properties. Mineral oil is added to the vesicles for osmotic stability.

The following examples will more clearly delineate the invention.

EXAMPLE 1

ENCAPSULATED MOISTURIZER

The encapsulated moisturizer is made by blending a lipid phase with an aqueous phase at sufficiently high shear rates to produce the paucilamellar lipid vesicles. In the preferred procedure, solvents for the lipids are unnecessary; the lipids are just heated to make them fluid and are reacted with the aqueous phase to make the lipid vesicles. The moisturizer is mixed with whichever phase it best blends into, normally the aqueous phase. The volumes in the following procedures are for a small production scale run, but large industrial production scale runs can also be used by modifying the amount of material.

A. Preparation of the Lipophilic Phase

Two different formulas are presently being used for the moisturizer of the invention. Although the batch sizes shown herein are unequal, any sized batch can be made by a scaling procedure.

(1) Approximately 2.92 kg of polyoxyethylene 2-cetyl ether (BRIJ 52-ICI Americas, Inc.) is mixed with 900 g cholesterol and 130 g oleic acid. Additional or different surfactants may be used in place of part or all of the BRIJ 52. The lipophilic phase is heated to approximately 65° C. in a mixing container to form a flowable lipid phase. This flowable lipid phase is maintained at an elevated temperature, while mixing continuously, to keep it homogeneous.

After blending the lipid, cholesterol and charge-producing oleic acid, approximately 4.73 kg of heated mineral oil (Drakeol 19 or 21, Penreco) is blended with the lipid phase at about 60° C. to form a homogenous suspension of the oil in the lipid. The mineral oil helps improve the osmotic stability of the vesicles upon formation.

(2) In the second procedure, approximately 25.8 kg glycerol monostearate, 19.5 kg polyoxyethylene 20 sorbitan monostearate (TWEEN 60), 10.9 kg cholesterol, and 1.15 kg oleic acid are blended at about 65° C. until melted and homogenous. About 63.1 kg of heated mineral oil is blended with the lipid for about 15 minutes at 60° C., forming the lipophilic phase.

B. Preparation of the Aqueous Phase

The aqueous phase is formed in two parts because of different temperatures needed for ingredient dissolution. Again, two different size batches (B1 and B2, corresponding to A1 and A2), are used, but scaling to any sized batch is possible.

(1) First, approximately 68 g of methylparaben and 7.57 g of propylparaben are dissolved in approximately 0.75 gal. of deionized water by continuously mixing at 90° C. until all of the ingredients are dissolved. The methylparaben and propylparaben are stabilizers and can be replaced by any other industrial stabilizer. Once all the stabilizers are dissolved, the mixture can be cooled to 50°–70° C.

The second portion of the aqueous phase is made by dissolving approximately 38.6 g of $KH_2PO_4$, 9.0 g NaOH, 210 g NaCl, and 3.79 kg LUBRAJEL (vaseline-type moisturizer, Guardian Chemical Co.) in about 5 gal. of the deionized water at 55°–65° C. LUBRAJEL is a standard external dog and cat skin and hair moisturizer. The salts are mixed first at about 65° C. and the LUBRAJEL is then added. These ingredients readily go into solution. The stabilizer portion of the aqueous phase is then added to the moisturizer portion and the volume is adjusted to approximately 7.5 gal.

(2) In this procedure, approximately 680 g methylparaben, 75.7 g propylparaben, and 7 gal. deionized water are heated to 90° C. and blended until dissolved. The mixture is cooled and set aside for addition to the remainder of the aqueous phase.

The second part of the aqueous phase contained about 340 g $KH_2PO_4$, 79.9 g NaOH, 1.87 kg NaCl, and 37.9 kg LUBRAJEL. The same mixing procedure as described above is then followed.

C. Formino the Lipid Vesicles

The previously formed lipid phase is maintained at approximately 50°–70° C. with continuous mixing while the aqueous phase is maintained approximately 50°–65° C., also with continuous mixing. The lipid and aqueous phases are pumped into a machine for formation of paucilamellar lipid vesicles manufactured by Micro Vesicular Systems, Inc. This lipid vesicle manufacturing machine has four inlet jets, two each for the lipid phase and the aqueous phase. Each inlet jet is directed to allow a substantially tangential flow of the liquid about a substantially cylindrical central chamber. The lipid and aqueous phases meet in the chamber, and the lipid vesicles are rapidly formed and removed through an axial outlet. The pump speeds for the two phases are adjusted to allow sufficient turbulence in the chamber to produce the high shear conditions needed for manufacture of these paucilamellar lipid vesicles. In an industrial production scale-up of the present Example, the flow rate for the lipid phase is approximately 530 ml/min. while the flow rate for the aqueous phase is approximately 4,200 ml/min.

The formed moisturizer-containing lipid vesicles can be collected and stored for use in any moisturizer-containing product.

EXAMPLE 2

MOISTURIZING SHAMPOO

In this Example, an industrial sized batch of the lipid vesicles formed in Example 1 are used in a otherwise relatively standard dog and cat shampoo to provide additional moisturizing. The shampoo formula has approximately 855 kg of MS-1 (Miranol Chemical Company, Inc.), a surfactant-sudsing shampoo base with polyethylene glycol derivative surfactants and sudsing agents added; 85.5 kg Mirataine CBS (cocamidopropyl hydroxysultaine, Miranol Chemical Company, Inc.), a sudsing agent; 8.5 kg each of Dowicil 200 (quaternium 15, Dow Chemical Company), a preservative, and a fragrance; and 171 kg of the encapsulated moisturizer. All of these ingredients are dissolved/suspended in approximately 450 gals. of deionized water to form the shampoo containing the encapsulated humectant.

EXAMPLE 3

MEDICATED SHAMPOO

In this Example, a coal tar shampoo useful as an antiseborrheic agent is made using the humectant lipid vesicles of the invention. The base for the coal tar shampoo is substantially the same as that produced in Example 2. Compounds MS-1, Mirataine CBS, Dowicil 200, and the lipid vesicles are added in the same amounts as in the Example 2 shampoo. In addition, approximately 51.3 kg of Coal Tar Topical Solution USP (Amend Drug & Chemical Co.) and 1.1 kg TWEEN 80 (polysorbate 80, ICI Americas, Inc.) are added. Because of the somewhat noxious smell of the coal tar solution, the fragrance level is raised to approximately 13 kg. The same 450 gals. of deionized water is used as the liquid in the shampoo, yielding approximately the same size shampoo batch.

The foregoing Examples are purely illustrative of the procedures and materials which can be used in the present invention and are expressly nonlimiting. Those skilled in the art will be able to determine additional products and procedures within the scope of the invention. Such other products and procedures are encompassed within the scope of the following claims.

What is claimed is:

1. An humectant for use in external animal care products comprising a moisturizer and mineral oil encapsulated in apaucilammelar lipid vesicle said lipid vesicle having a nonphospholipid surfactant selected from the group consisting of glycerol monostearate, glycerol monooleate, and polyoxyethylene sorbitan oleates, palmitates, and stearates as its major lipid component.

2. The humectant of claim 1 wherein said paucilamellar lipid vesicle further comprises a sterol.

3. The humectant of claim 2 wherein said sterol is selected from a group consisting of cholesterol and its active fragments.

4. The humectant of claim 1 wherein said paucilamellar lipid vesicle further comprises a charge producing agent.

5. A shampoo for pet care comprising an humectant and an active cleaning ingredient, said humectant having a moisturizer and mineral oil encapsulated in a paucilamellar lipid vesicle said lipid vesicle having a nonphospholipid surfactant selected from the group consisting of glycerol monostearate, glycerol monooleate, and polyoxyethylene sorbitan oleates, palmitates, and stearates as its major lipid component.

6. The shampoo of claim 5 wherein said paucilamellar lipid vesicle further comprises a sterol.

7. The shampoo of claim 6 wherein said sterol is selected from a group consisting of cholesterol and its active fragments.

8. The shampoo of claim 5 wherein said paucilamellar lipid vesicle further comprises a charge producing agent.

9. A cream rinse for pet care comprising an humectant and an active hair conditioning agent, said humectant having a moisturizer and mineral oil encapsulated in a paucilmallear lipid vesicle said lipid vesicle having a nonphospholipid surfactant selected from the group consisting of glycerol monostearate, glycerol monooleate, and polyoxyethylene sorbitan oleates, palmitates, and stearates as its major lipid component.

10. The cream rinse of claim 9 wherein said paucilamellar lipid vesicle further comprises a sterol.

11. The cream rinse of claim 10 wherein said sterol is selected from a group consisting of cholesterol and its active fragments.

12. The cream rinse of claim 9 wherein said paucilamellar lipid vesicle further comprises a charge producing agent.

13. An humectant for use in animal care products, said humectant in the form of a paucilamellar lipid vesicle comprising a polyoxyethylene fatty ether, cholesterol, and oleic acid, said paucilamellar vesicle encapsulating a moisturizer and mineral oil.

14. The humectant of claim 13 wherein said polyoxyethylene fatty ether is selected from a group consisting of polyoxyethylene lauryl ethers and polyoxyethylene cetyl ethers.

15. The humectant of claim 13 wherein said paucilamellar lipid visicle further comprises a sterol.

16. The humectant of claim 15 wherein said sterol is selected from the group consisting of cholesterol and its active fragments.

17. The humectant of claim 13 wherein said paucilamellar lipid vesicle further comprises a charge producing agent.

18. A humectant for use in cream rinses and shampoos for pet care, said humectant in the form of a paucilamellar lipid vesicle comprising glycerol monostearate, polyoxyethylene 20 sorbitan monostearate, cholesterol, and oleic acid, said paucilamellar lipid vesicle encapsulating a moisturizer.

19. The humectant of claim 18 wherein said paucilamellar lipid vesicle further comprises mineral oil.

* * * * *

UNITED STATES PATENT AND TRADEMARK OFFICE
CERTIFICATE OF CORRECTION

PATENT NO. : 4,942,038

DATED : July 17, 1990

INVENTOR(S) : Donald F. H. Wallach

It is certified that error appears in the above-identified patent and that said Letters Patent is hereby corrected as shown below:

At Column 4, line 32, delete "Formino" and insert --Forming--.

At Column 5, line 36, delete "apaucilammelar" and insert --a paucilamellar--.

Signed and Sealed this

Seventh Day of July, 1992

Attest:

DOUGLAS B. COMER

Attesting Officer

Acting Commissioner of Patents and Trademarks